United States Patent [19]

Loo et al.

[11] Patent Number: 5,003,980
[45] Date of Patent: Apr. 2, 1991

[54] METHOD AND APPARATUS FOR MEASURING LUNG DENSITY BY COMPTON BACKSCATTERING

[75] Inventors: Billy W. Loo, Oakland; Frederick S. Goulding, Lafayette, both of Calif.

[73] Assignee: The United States of America as represented by the United States Department of Energy, Washington, D.C.

[21] Appl. No.: 470,420

[22] Filed: Jan. 29, 1990

Related U.S. Application Data

[63] Continuation of Ser. No. 167,207, Mar. 11, 1988, abandoned, which is a continuation-in-part of Ser. No. 788,459, Oct. 17, 1985, abandoned.

[51] Int. Cl.⁵ .............................................. A61B 6/00
[52] U.S. Cl. .................... 128/653 R; 128/716; 378/89
[58] Field of Search ............... 128/653 R, 716, 659; 378/86, 89; 250/363.01, 363.02, 363.07

[56] References Cited

U.S. PATENT DOCUMENTS

| | | | |
|---|---|---|---|
| 2,997,586 | 8/1961 | Scherbatskoy | 378/89 |
| 3,183,351 | 5/1965 | White | 378/89 |
| 3,470,372 | 9/1969 | Bayly | 378/89 |
| 3,961,186 | 6/1976 | Leunbach | 378/90 |
| 4,123,654 | 10/1978 | Reiss et al. | 378/89 |
| 4,224,517 | 9/1980 | Lubecki et al. | 378/47 |

FOREIGN PATENT DOCUMENTS 0240076 10/1986 Fed. Rep. of Germany ........ 378/89

Primary Examiner—Ruth S. Smith
Attorney, Agent, or Firm—L. E. Carnahan; Roger S. Gaither; William R. Moser

[57] ABSTRACT

The density of the lung of a patient suffering from pulmonary edema is monitored by irradiating the lung by a single collimated beam of monochromatic photons and measuring the energies of photons Compton backscattered from the lung by a single high-resolution, high-purity germanium detector. A compact system geometry and a unique data extraction scheme are utilized to monimize systematic errors due to the presence of the chestwall and multiple scattering.

37 Claims, 6 Drawing Sheets

METHOD AND APPARATUS FOR MEASURING LUNG DENSITY BY COMPTON BACKSCATTERING

BACKGROUND OF THE INVENTION

This invention was made with Government support under Department of Energy Contract No. DE-AC0376SF00098. The Government has certain rights in this invention.

This application is a continuation of Ser. No. 07/167,207 filed Mar. 11, 1988, now abandoned, which is a continuation-in-part of U.S. application Ser. No. 788,459 filed Oct. 17, 1985, now abandoned, and is assigned to the same assignee as the parent application.

This invention relates to the measurement of lung density and more particularly to a method and apparatus for monitoring lung density of a patient suffering from pulmonary edema by measuring Compton back-scattered photons.

Pulmonary edema is the pathological increase of water in the lung found most often in patients with congestive heart failure and other critically ill patients who suffer from intravenous fluid overload. No present technique, simple or complicated, exists for the accurate in vivo determination of lung water. A good indicator of lung water is an accurate measurement of absolute lung density in a homogeneous region of the lung free of large blood vessels. Current medical diagnoses largely rely on the chest x-rays, but roentgenograms are neither quantitative nor sensitive to even moderate changes in lung density. Among various non-invasive techniques, Compton scattering seems to hold the most promise, but traditional technique for dealing with the problem of attenuation along the beam path requires the simultaneous measurements of transmitted and scattered beams. Since multiple scattering is a strong function of the density of the scattering medium and the mass distribution within the detection geometry, there are inherent uncertainties in the system calibration unless it is performed on a body structure closely matched to that of each individual patient.

As will be explained more in detail below, other researchers who have employed Compton scattering techniques generally use systems of extended size and detectors with poor energy resolution. This results in significant systematic biases from multiple-scattered photons and larger errors in counting statistics at a given radiation dose to the patient.

Substantial effort has been directed to using the Compton effect for determining the density of electrons, fluids, or gases in the interior of materials or bodies. These prior efforts are exemplified by U.S. Pat. Nos. 2,997,586 issued Aug. 22, 1961 to S.A. Scherbatskoy; U.S. Pat. No. 3,183,351 issued May 11, 1965 to D. F. White; U.S. Pat. No. 3,470,372 issued Sept. 30, 1969 to J. G. Bayly; U.S. Pat. No. 3,961,186 issued June 1, 1976 to I. Leunbach; U.S. Pat. No. 4,123,654 issued Oct. 31, 1978 to Reiss et al; and U.S. Pat. No. 4,224,517 issued Sept. 23, 1980 to A. Lubecki et al. The above identified prior approaches are either not concerned with or are not capable of accurately determining the density of the lung behind a chestwall of unknown thickness and composition. These above-exemplified approaches have resorted to the measurement of absolute count rate whether they were transmission or Compton scattering measurements, and such approaches cannot resolve the problem involving absorbers, such as the chestwall, in the beam paths.

For example, the two-source-two-detector method of above-referenced patent to Leunbach, which is concerned with determination of the electron density of small volumes of a body, may in principle correct for unknown absorptions but in reality has tremendous difficulties. The necessity to rotate the body or the apparatus between two consecutive sets of measurements make the relocation of the target and the replication of the absorption paths difficult. Also, the need to make transmission measurements dictates the size of the apparatus which must accommodate the body. Such a large system results in a large amount of systematic error because multiple scattering varies significantly with the size and mass distribution of the body, and the radiation dose will be higher at a given level of counting statistics needed.

The useful energy range of a practical gamma ray source is much more restrictive than those proposed and used in the prior art. Below 100 keV, besides the problem of absorption by the bones in the chestwall, the spread of the scattered photon energies will be too narrow to be adequately resolved even with HPGe detectors. Above 200 keV, the efficiency of total absorption in Ge detectors decreases rapidly, and the spectral quality will suffer due to poor peaks-to-Compton ratios. At still higher energies, radiation shielding becomes an increasingly difficult problem, leading to very bulky and clumsy source holders. The high energy radiation leakage will also contribute significantly to the spectral background of the detector.

While the prior approaches may have limited success in their attempts to measure lung density, notwithstanding their inherent systematic errors and the need for a standby cyclotron or nuclear reactor to produce the special sources required, none have resulted in a practical instrument for accurate routine measurement of lung density. Thus, a need exists for an instrument capable of providing accurate routine lung density measurements, particularly such an instrument which is compact and easily portable for monitoring the course of pulmonary edema at a hospital bedside or at an out-patient clinic.

It is therefore an object of the present invention to provide a method and apparatus for providing fast and direct information on the density of the lung.

It is another object of the present invention to provide a non-invasive, accurate, sensitive and comparatively inexpensive method and apparatus for measuring lung density.

It is still another object of the present invention to provide a compact, easily portable apparatus for monitoring the course of pulmonary edema at the hospital bedside or out-patient clinics.

It is a further object of the present invention to provide a method and apparatus for measuring lung density non-invasively while subjecting the patient to radiation exposure risk much less than the standard chest x-ray.

The above and other objects are achieved by the present invention which discloses a method and apparatus for monitoring the density of the lung by measuring Compton backscattered photons in a compact system geometry with a high resolution detector such as a high purity germanium detector. By proper design and a unique data extraction scheme, effects of the variable chest wall on lung density measurements are minimized.

SUMMARY OF THE INVENTION

The invention is directed to a simple clinical instrument referred to herein as a Compton densitometer, that can routinely monitor the degree of pulmonary edema as a guide to detection, proper treatment and prognosis relating to, for example, congestive heart failure, intravenous fluid overload, drug overdose, lung injections, and chest and head injuries. In addition, the instrument can be used to evaluate the efficiency of therapy in clinical research.

The instrument of this invention provides for direct lung density measurements using only Compton back-scattered photons in spite of the presence of a chest wall. Employing a one-source, one-detector system geometry of this invention minimizes the effect of multiple scattering and reduces the amount of radiation required. The use of a high-resolution, high-purity germanium (HPGe) detector not only allows for defining target volumes from photon energies but also helps to reject multiple scattered photons. These factors acting in concert provide a clinical lung density monitor that is inherently more accurate than prior known approaches, while also having portability, cost and safety factors not previously provided.

Basically, the invention involves a method and an apparatus for measuring lung density. The method comprises a non-invasive approach involving irradiating a target lung with a collimated beam of monochromatic photons in the range of 100–200 keV, measuring the energies of the photons backscattered by the target lung, determining the relative intensities of the scattered photons at successive points along the incident beam within the target lung, determining the attenuation constant of the target lung from the relative intensities, and determining the density of the target lung from the attenuation constant. The apparatus comprises a source for irradiating a target lung with a collimated beam of monoenergetic photons, a detector for measuring relative intensities of photons from the source Compton backscattered at different angles in the target lung, the source and detector being configured to provide lung density measurement that is insensitive to the presence of a chest wall and positioned such that the collimated beam passes a selected range of distance from the detector.

The accompanying drawings, which are incorporated in and form a part of the specification, illustrate the present invention and, together with the description, serve to explain the principles of the invention.

DESCRIPTION OF THE INVENTION

The invention is a non-invasive lung density monitor for clinical use that is accurate, easily portable, safe and inexpensive. The monitor, referred to herein as a (Compton densitometer) of this invention involves measuring only Compton back-scattered photons in a compact system geometry with a high resolution germanium detector, and using a unique data extraction approach, whereby systematic effects of multiple scattering and the variable chest wall are minimized.

Figure 1:
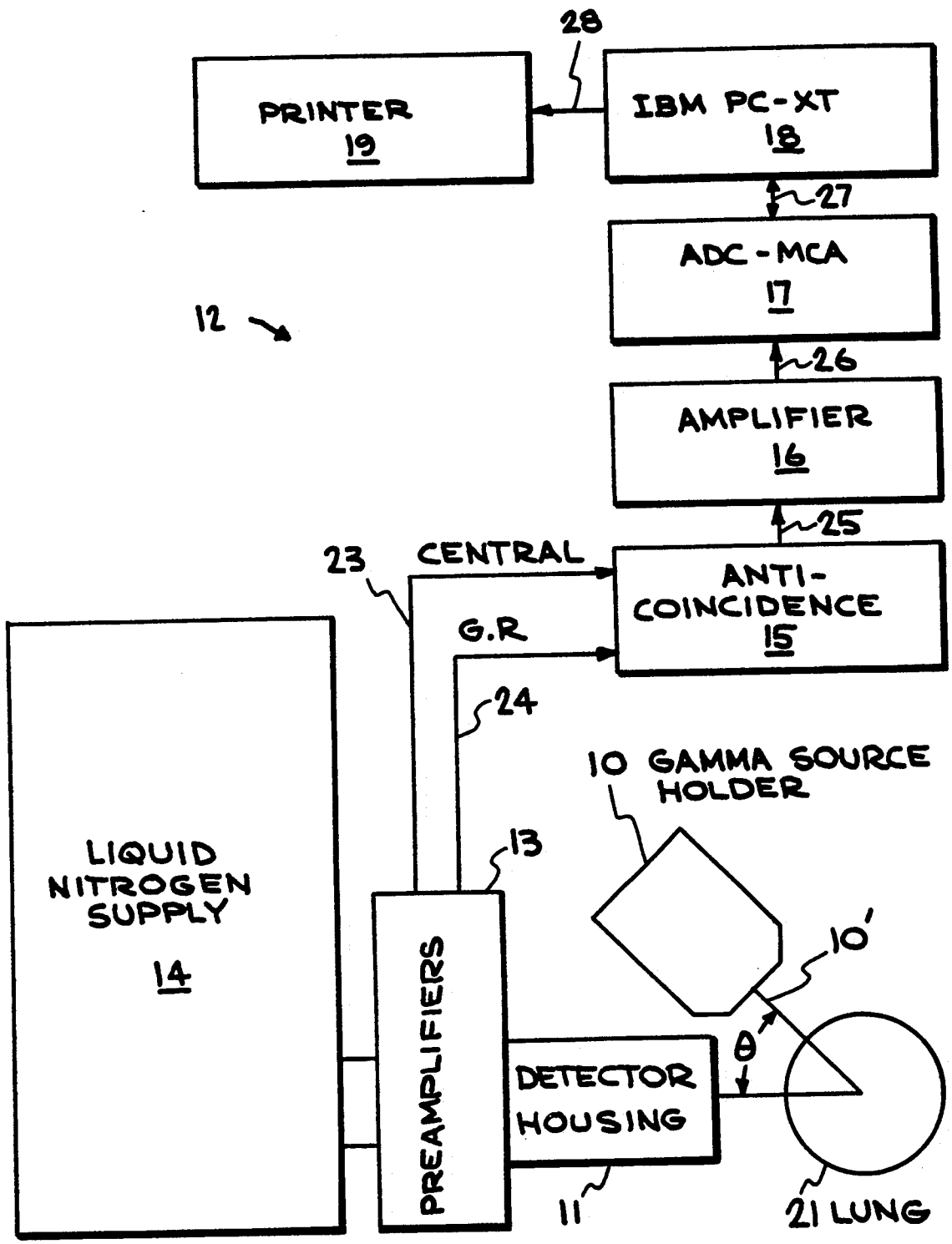
FIG. 1 is a block diagram which shows the components of a total system of an embodiment of a lung density measurement apparatus (Compton densitometer) of the invention.

FIG. 1 illustrates in block component format an embodiment of a total system or densitometer made in accordance with the invention. Basically, the system comprises a gamma source within a holder 10, a detector 11 operatively connected to a conversion apparatus or mechanism generally indicated at 12. The conversion apparatus 12 in this embodiment comprises preamplifiers 13 connected to receive input from detector 11, a liquid nitrogen dewar 14, with output signals from preamplifiers 13 fed into standard electronics components 15, 16 and 17, and the data fed into a personal computer 18 and to a printer (readout) 19. The function of the system is more fully recognized in conjunction with FIGS. 2 and 3 wherein a collimated beam 10' of photons from a gamma source within holder 10 is directed through an entrance point of a wall 20, such as the chestwall of a patient into a lung 21 of a patient and photons indicated at 23 in the beam 10' Compton backscattered in lung 21 pass through an exit point of wall 20 into detector 11.

Figure 2:
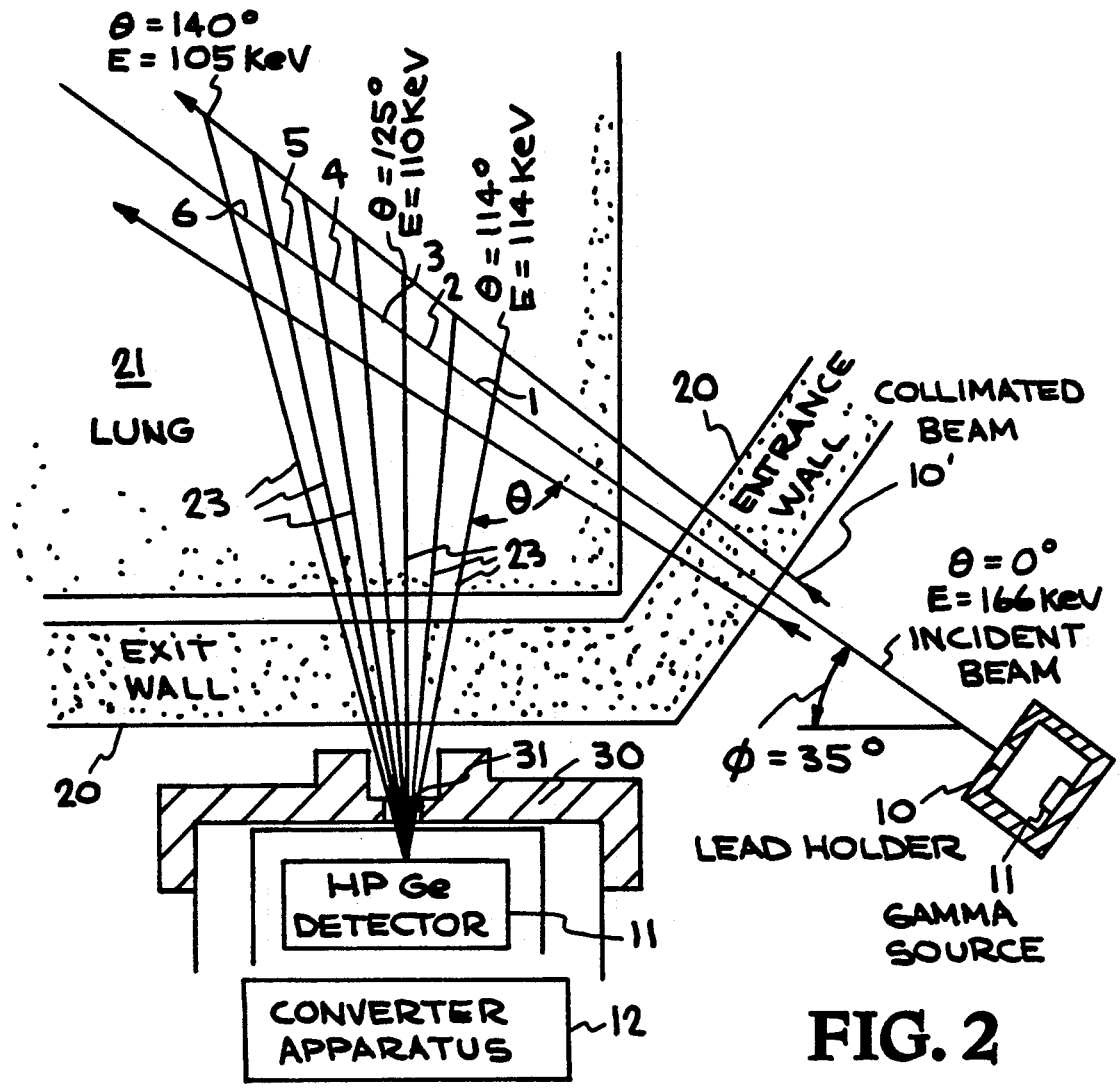
FIG. 2 is a schematic drawing for explaining the principle of the present invention.
Figure 3:
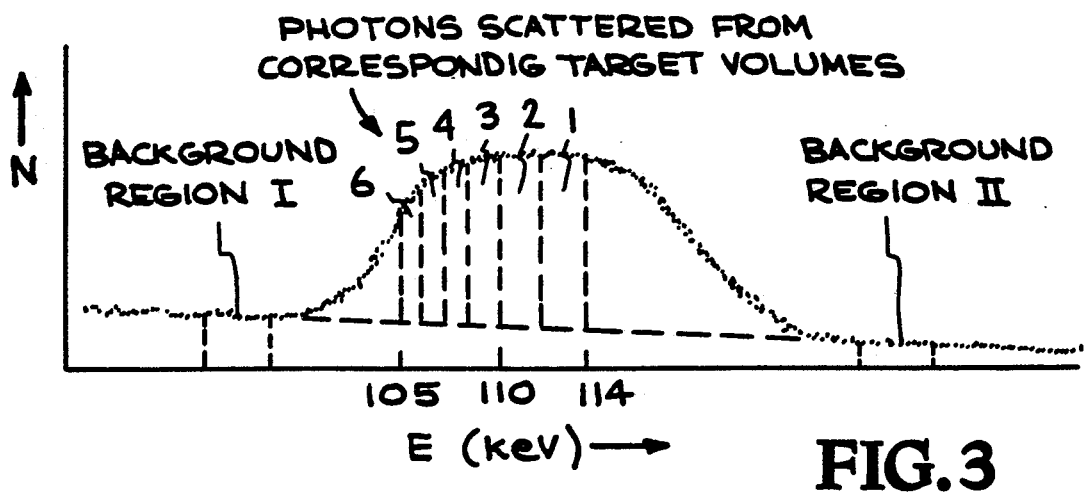
FIG. 3 is a typical energy spectrum obtained from the experimental system of FIG. 2.
Figure 11:
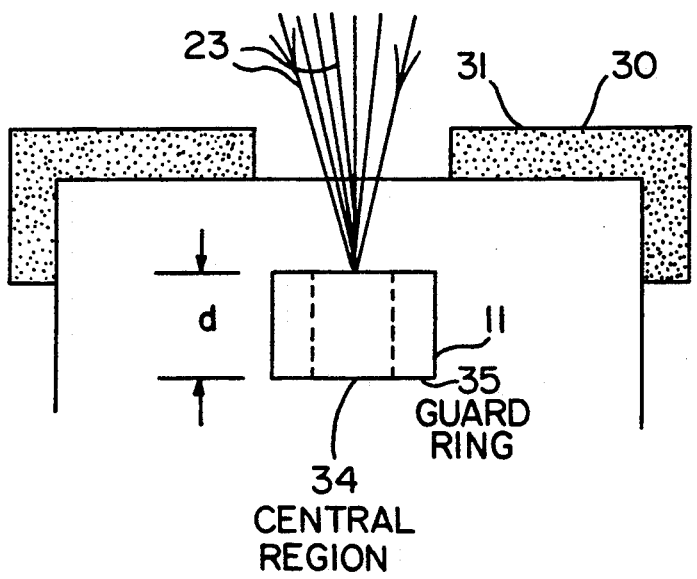

In the embodiment illustrated in FIGS. 1–3, the detector is a high-purity germanium (HPGe) detector consisting of a central region surrounded by an active guard-ring, such as illustrated in FIG. 11. As seen in FIG. 1, signals 23 from the central region of detector 11 are processed by device 15 in anticoincidence with signals 24 from the guard ring (G.R.) section of detector 11 to better define the system geometry and to reduce spectral background. As an example, the device 15 may be composed of an anticoincidence circuit which blocks any output signal if input signals 23 and signals 24 are simultaneously present. The surviving signals 25 are then amplified at amplifier 16 and signals 26 therefrom are further processed by an analog-to-digital converter (ADC) and multi-channel analyzer (MCA) indicated at 17. Further data handling and calculations are performed by a personal computer (PC) 18 such as an IBM-PC-XT which receives signals 27 from device 17. The results are finally displayed on the PC 18 monitor, outputted via the printer 19 as indicated by signals 28, or stored on magnetic discs (not shown). The components 13–19 are conventional off-the-shelf components and need not be described in greater detail.

The gamma source holder 10, in which a point source 10" is enclosed, produces the collimated beam 10' of gamma rays. This beam, in the case of a CE-139 source, consists of a clean primary monoenergetic line at 166 keV together with some lower energy x-rays which are of no consequence. In the embodiment of FIG. 2, the beam 10' has an initial diameter of 5 mm and a half-angle divergence of 50 mm. The beam 10' makes an angle $\phi$ with the front surface of the detector 11, which in the FIG. 2 embodiment is 35°.

The overall system geometry is further illustrated in FIG. 2 and described in greater detail hereinafter. After penetrating the entrance chest wall 20, the incident beam 10' is directed through a selected uniform portion of lung 21. The HPGe detector 11 measures the energies and intensities of the photons 23 that are scattered along the path of beam 10' which are subsequently stopped in the central region of detector 11. The average scattering angle $\theta$ (FIG. 2) is related to the energy of the detected photon 23 by the Compton formula:

$$E = E_o / \left( 1 + \frac{E_o}{511} (1 - \cos\theta) \right)$$

where $E_o$ and E are, respectively, the incident and scattered photon energies in keV.

Symbolically, the count-rate per unit distance along the incident beam dN/dX is expressed as:

$$dN/dX = (dN/dE)(dE/d\theta)(d\theta/dX)$$

where dN/dE is the energy spectrum of count-rate N vs E, $dE/d\theta$ is a scaling factor relating E and $\theta$ as given by the Compton formula, and $d\theta/dX$ is another scaling factor relating $\theta$ and the distance X along the incident beam 10' as determined by the system geometry.

Thus, from a typical spectrum as shown in FIG. 3, the counts scattered from each successive centimeter along beam 10' (e.g., those labeled 1-6) can be identified after appropriate calculation and background subtraction via the converter apparatus 12.

We have found experimentally that within a certain range of incident angles (20°<$\theta$<60°), where $\theta$ is the angle between beam 10' and the front surface of detector 11 as seen in FIG. 2, and a certain range of scattered angles (90°<$\theta$<160°), the decrease in count-rate (N) per unit distance along the beam path can be represented by a simple exponential:

$$N = N_o \exp(-KX)$$

Where $N_o$ is the intercept slope parameter, K is the attenuation constant or slope parameter, and X is the distance along the beam in cm.

This equation is a reasonable description of experimental results that is valid over a limited range of geometric variables indicated above, and is not derivable from first principles. Because of the complex dependency of the scattering process on energy, angular distribution, and other geometrical parameters, the similarity between this equation with that of describing the attenuation of a beam by a thin wall is accidental.

Figure 4:
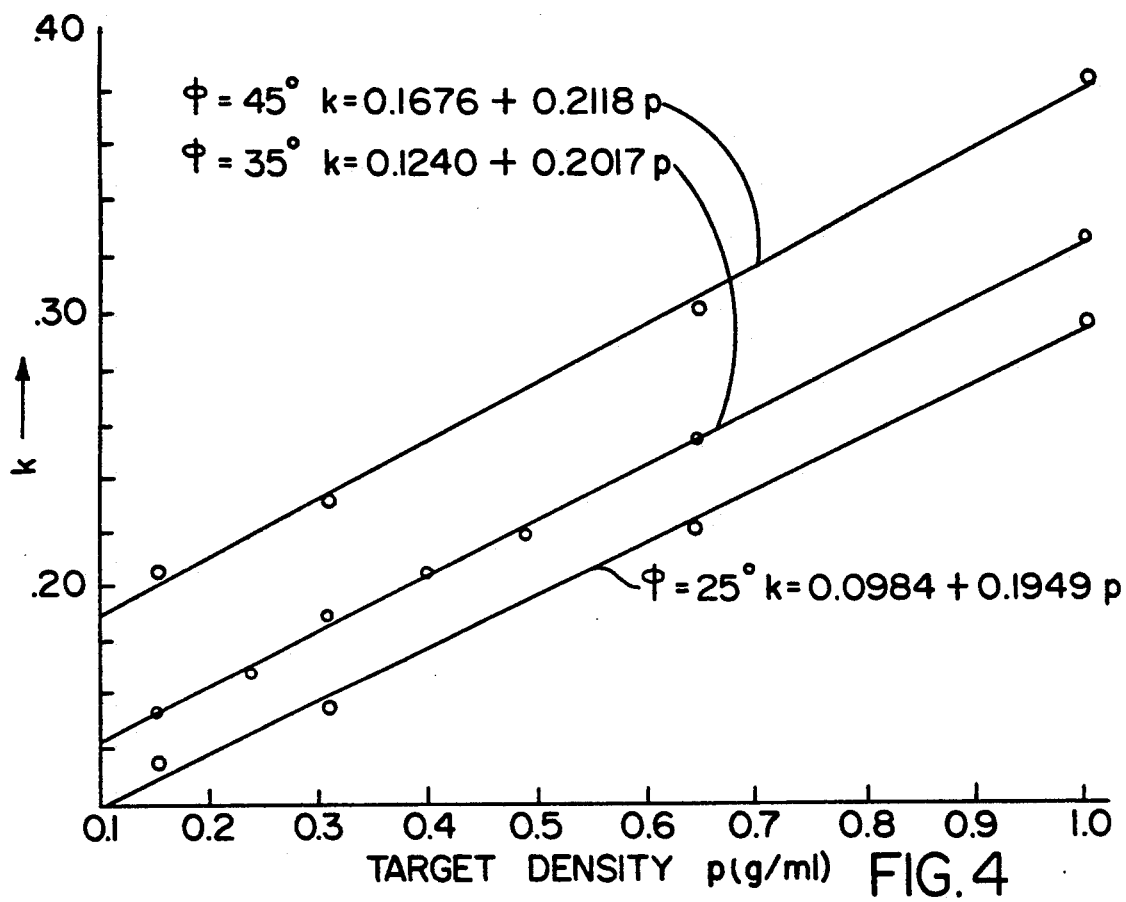
FIG. 4 is a calibration curve showing the relationship between the attenuation constant (k) and the lung density ($\rho$).

We have further found that the slope K in a lnN vs X plot is linearly dependent on the target density $\rho$ and virtually unaffected by the presence of absorbers such as the chestwall 20 which only tends to reduce $N_o$. Explicit calibration curves K vs can then be generated. FIG. 4 shows that such linear relationships generally hold true for $\theta$ in the range of 25°-45° and $\rho$ in the range of 0.1-1.0. The significance of this unique method of density determination is that there is no need to be concerned with absolute counts; only the relative counts (1-6) from one centimeter to the next along the incident beam 10' are important. A relative count or point is defined as one region of the lung with respect to adjacent regions of the lung.

The problem of determining lung density is therefore reduced to that of finding the slope K from a linear regression of the count-rates from, say, six centimeter intervals which constitute the target volume. In the example given in FIG. 3, this corresponds to analyzing the counts in the energy intervals of 105-114 keV scattered from a 166 keV beam.

Table 1 summarizes the evidence that the slope K hence density $\rho$ so determined is insensitive to the presence of the chestwall. In this table, for a given combination of $\phi$ and $\rho$, $K_O$ represents the slope measurement on a target of known density without the chestwall, and $K_1$ is the measured slope of the same target when 19 mm of plastic absorbers (to simulate a chestwall) were inserted both in the entrance and the exit beams.

The difference in density determinations between these two measurement conditions without any corrections is denoted by $\Delta\rho$. For example, in the most favorable geometry in which 0=45°, the systematic errors are typically under 0.02 g/ml for most densities of interest (i.e., in the range of 0.1-0.7 g/ml).

| $\phi$ | $\rho$(g/ml) | .156 | .311 | .644 | 1.00 |
|---|---|---|---|---|---|
| | $K_0$ | .1341 | .1541 | .2207 | .2960 |
| 25° | $K_1$ | .1466 | .1661 | .2297 | .2994 |
| | $K_1/K_0$ | 1.093 | 1.078 | 1.041 | 1.011 |
| | $\Delta\rho$(g/ml) | 0.064 | 0.062 | 0.046 | 0.017 |
| 35° | $K_0$ | .1533 | .1892 | .2541 | .3251 |
| | $K_1$ | .1611 | .1929 | .2539 | .3299 |
| | $K_1/K_0$ | 1.051 | 1.020 | 0.999 | 1.015 |
| | $\Delta\rho$(g/ml) | 0.039 | 0.019 | −0.001 | 0.024 |
| | $K_0$ | .2047 | .2313 | .2988 | .3829 |
| 45° | $K_1$ .2088 | .2326 | .2974 | .3758 | |
| | $K_1/K_0$ | 1.020 | 1.006 | 0.995 | 0.981 |
| | $\Delta\rho$(g/ml) | 0.019 | 0.007 | −0.007 | −0.034 |

With the basic principle of the invention having been described, reference is again made to FIG. 2 wherein numeral 21 indicates a uniform region of a target lung. Numeral 20 indicates a section of a chestwall of a patient. The collimated beam 10" of photons at 166 keV from photon source (gamma source) 10, mounted within a lead holder or housing 10 is made incident through the chestwall 20 into the lung 21. Note that in this embodiment, the incident beam 10' is at the angle $\theta$ of 35° with respect to the front surface of detector 11. The detector 11 is of a high-purity germanious (HPGe) type and is positioned outside the chestwall 20 such that the photons 23 of incident beam 10' which are Compton backscattered in lung 21 are monitored. A shield 30 of lead or tantalum having and opening 31 is placed in front of detector 11 to suppress multiple-scattered photons reaching the detector 11, as described below.

Figure 9:
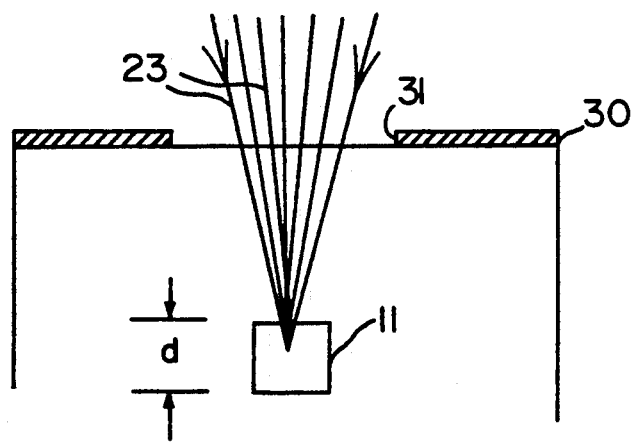
FIGS. 9, 10 & 11 schematically illustrate embodiments of detectors for use in the invention.
Figure 10:
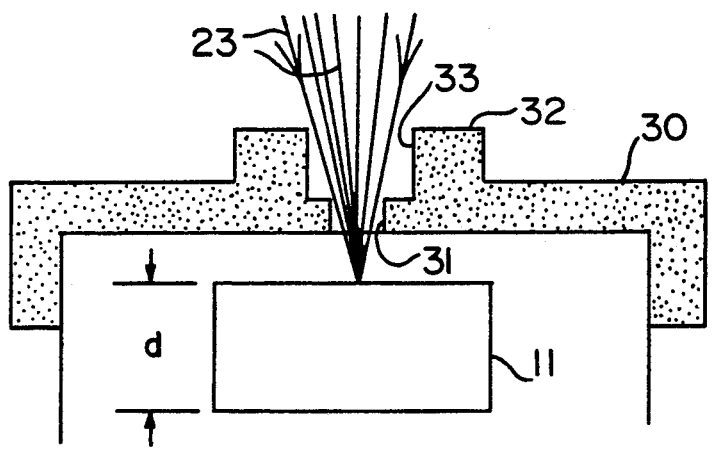

The design or configuration detector 11 depends on the application for the invention. FIGS. 9, 10 and 11 illustrate three configurations that have been successfully employed in experimental verification of the invention. Note, that unlike systems which use detectors of inferior energy resolution, the lead or tantalum shields 30 placed in front of the detectors 11 are not used as collimators to define the target (lung). These shields are intended to stop multiple scattered events which do not originate in the target lung from reaching the detector. Although some multiple scattered photons can still reach detector 11 through opening 31 in shield 30, a significant portion of them will be rejected due to the high energy resolution of the detector.

As seen in the FIG. 9 embodiment, the detector 11 is of a 9 mm by 9 mm configuration with a depth d of 9 mm, with the shield 30 being made of tantalum with a thickness of 2 mm and an opening 31 of 3 cm.

The embodiment of FIG. 10, illustrates a detector of a 35 mm diameter with a depth d of 17 mm, using a lead shield 30 of similar construction to that of FIG. 2, with a thickness of −6mm and an opening 31 of 6 mm by 19 mm. Note that the shield of FIGS. 2 and 10 include an outwardly protruding section 32, having a diameter of 32 mm and length of 6 mm, with an opening 33 having a cross section of 12 mm by 25 mm, which functions to further prevent multiple scattered photons from reaching the detector 11.

The FIG. 11 embodiment utilizes a detector 11 of a 10 mm by 30 mm configuration with a depth d of 14 mm, and having a central region 34 and a guard ring (G.R.) 35, as described above with respect to FIG. 1. The central region 34 and guard ring 35 are both 14 mm thick. The shield 30 is made 10 of lead with a thickness of 6 mm, and opening 31 is of 25 mm diameter.

Each of the detectors 11 of FIGS. 9–11, like the detector of FIG. 2, is made of high purity germanium (HPGe) and thus function to reject a significant portion of any multiple scattered photons reaching the detector due to the high energy resolution thereof.

As discussed above, a typical energy spectrum detected by detector 11 of FIG. 2 is illustrated in FIG. 3, where N represents the scattered count-rate per unit distance along the incident beam 10', and E is the energy in keV. The angle of Compton-scattered photons and their energy are related by the Compton formula set forth above, and are also related by:

$$1/E_s = 1/E_i + (1 - \cos\theta)/E_e \text{ or } E_s = \frac{E_i}{1 + \frac{E_i}{E_e}(1 - \cos\theta)}$$

where $\theta$ is the scattering angle relative to the incident beam 10', $E_s$ is the energy of the scattered photons, $E_i$ is the energy of the incident radiation, and $E_e$ (or 511 keV) is the rest energy of an electron. As discussed above, FIG. 3 shows the numbers of photons scattered from different areas (1–6) inside target lung 21 along the path of incident beam 10'.

Consider, for example, the six areas (1–6), as shown in FIG. 2, representing scattering volumes at intervals of 1 cm along the incident beam 10' penetratings a selected portion of lung 21. With the incident beam 10' at an energy of 166 keV, those photons 23 scattered in the area "1" and detected by detector 11 have energies between 111.5 keV and 113.7 keV corresponding to scattering angles $\theta$ between 120° and 114°. Those photons 23 scattered in the area "6", similarly, have energies between 105.4 keV and 106.2 keV corresponding to scattering angles $\theta$ between 140° and 137°. Thus, the area under the curve in FIG. 3 may be divided by vertical lines into sections so that each section represents contributions from photons scattered in one of the numbered areas of FIG. 2. As shown in FIG. 3, a simple background subtraction may be performed by linear interpolation from count-rates in asymptotic regions I and II near each end of the energy spectrum.

Where the energy of incident beam 10' is, for example, 122 keV, those photons scattered in the area "1" and detected by the detector 11 have energies between 91 keV and 93 keV corresponding to scattering angles between 115° and 108°. Those scattered in the area "6", similarly, haVe energies between 85.9 keV and 86.6 keV corresponding to scattering angles between 139.1° and 135.5°.

Figure 5:
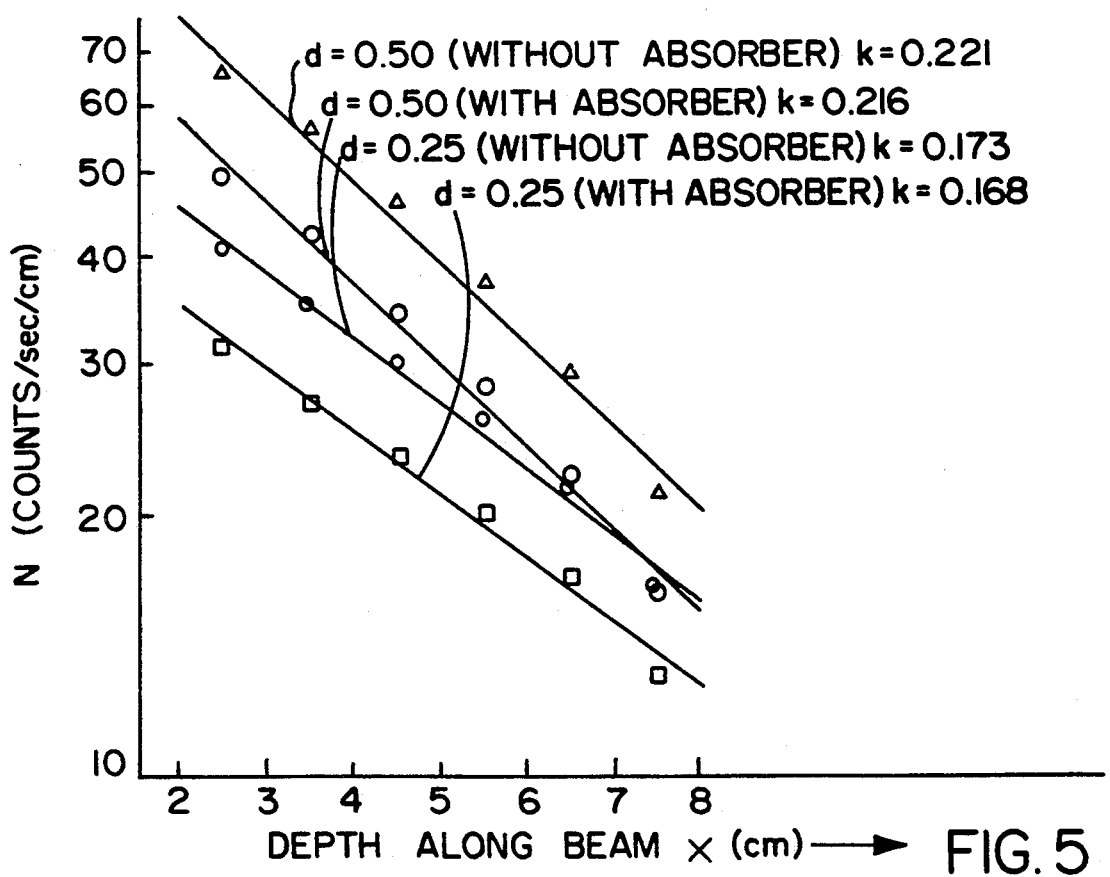
FIG. 5 is a graph which shows the relationship between the count rate per path length and the distance along the beam path.

It has been found experimentally that in certain geometrical configuration and within certain range of target locations, the scattered count rate per unit distance along the incident beam decreases exponentially with the traveled distance x, or $N = Ae^{-kx}$ where N is the number of detected photons, k is the attenuation constant, and A is a constant proportional to the number of incident photons and dependent on other physical and geometrical parameters. When N is plotted on a logarithmic scale against x, it is seen as shown in FIG. 5 that the negative slope, which represents the constant k, is insensitive to the presence of the chest wall 20, the presence of chest wall 20 affecting only the absolute count rates. The relative count rate from one target region to a succeeding region along the incident beam 10' remains essentially unchanged. In other words, the presence of absorbers such as the chest wall 20 only tends to lower the counting curve but does not affect the slope. As discussed above, it was further determined experimentally that k is a sensitive and linear function of target density within the range of specific gravities from 0.19 to 1.0 as shown in FIG. 4. Thus, a calibration curve of FIG. 4 enables one to make a direct determination of the lung density, unhampered by the presence of the chest walls.

Figure 6:
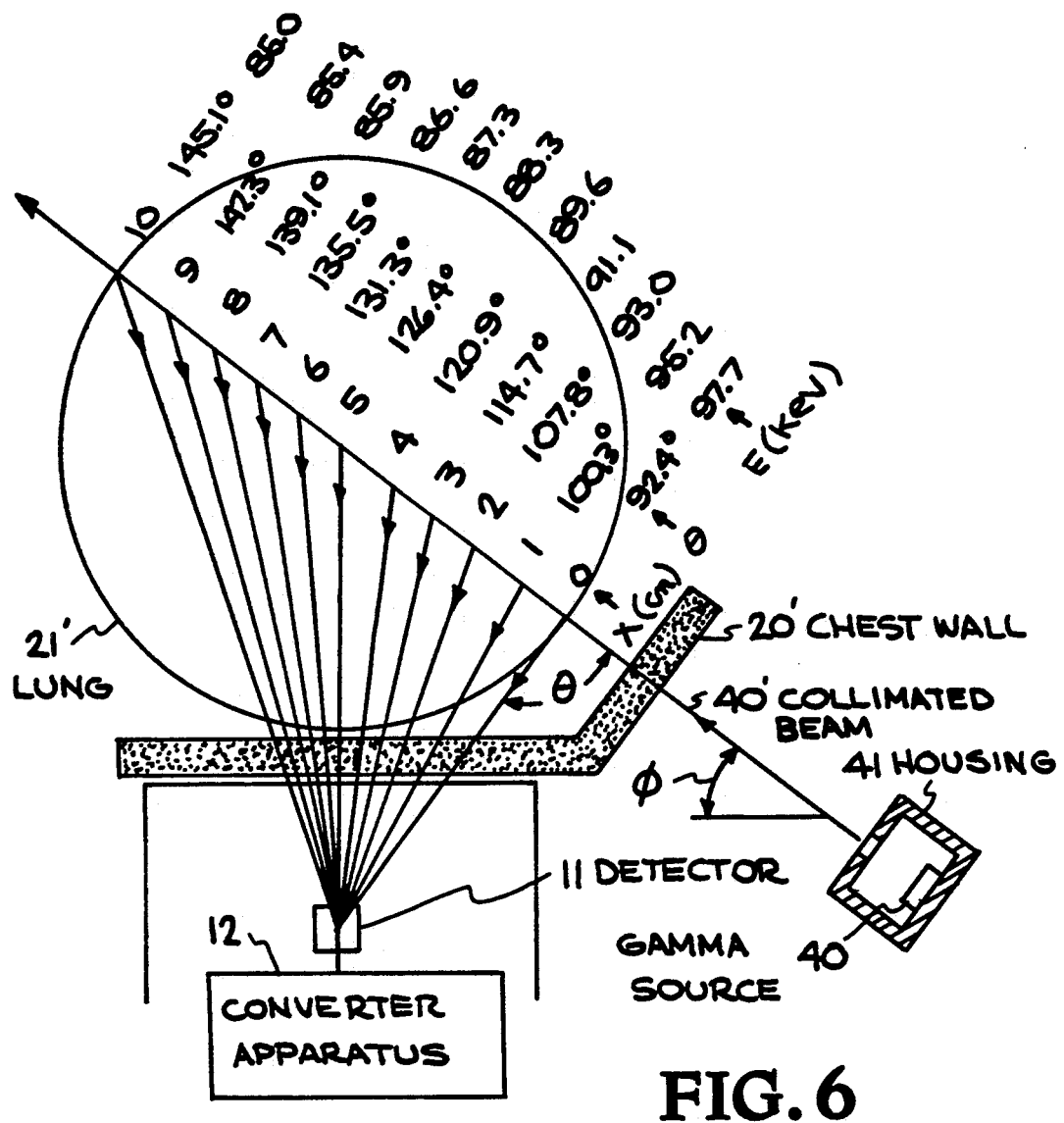
FIG. 6 is an experimental system according to another embodiment of the present invention.

Reference now being made to FIG. 6, wherein the same numerals as used in FIG. 2 are used to indicate like components, a weak $Co^{57}$ source 40 (5mCi)- with a diameter of 3 mm is mounted in a lead housing 41. A 5 mm hole in a tantalum collimator produces a gamma ray beam 40' with a half angle divergence of 50 mr. The diameter of the beam at the focal point of the detection system 11 is about 1.4 cm. A phantom 21', simulating a lung, consisting of a thin metal can 10 cm in diameter and 10 cm in height is used to represent a uniform volume of the lung. The effect of the chest wall 20' is simulated by a 6.5 mm plexiglas layer which intercepts the incident and exit beams. The density $\rho$ of the "lung" within the can 21' may be varied from 0.19 to 1.0 g/ml by mixing an appropriate amount of sawdust and water. The aforementioned beam of gamma rays is directed through the center of the can 21' at an angle $\theta$ of 35° with respect to the front of the detector housing 11', intended to be parallel to the chest wall 20'. The scattering volume along the narrow beam 40' is viewed by high-purity germanium detector 11 of which the effective center is about 9 cm from that of the can (lung) 21'. The scattering angles at various depths x along the beam 40' are indicated in FIG. 6 together with the photon energies at these scattering angles.

Figure 7:
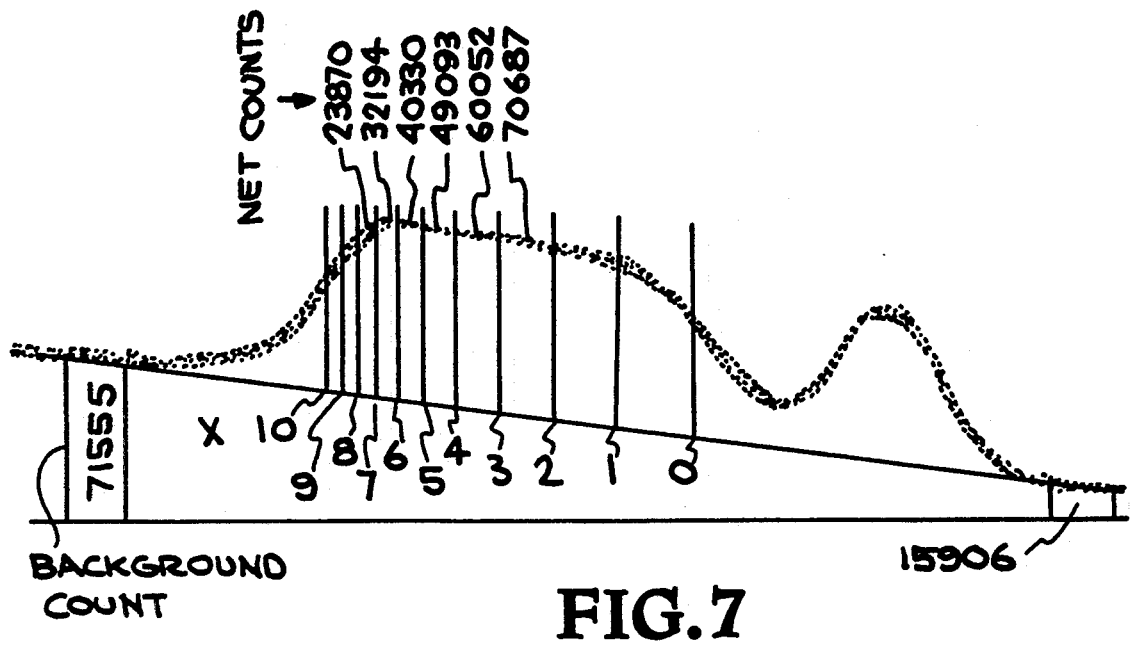
FIG. 7 is an energy spectrum obtained from the experimental system of FIG. 6.

FIG. 7 is an example of spectrum accumulated over a long period (1430 minutes) to show the distribution of the counts from regions at various depths x along the beam. The aforementioned method of subtracting the background effects by linear interpolation is effected and the net counts from each centimeter interval near the center of the scattering volume (x=2 to 8 cm) are used in a linear regression analysis to determine k. The peak to the right of the region of interest is due to scattering from the entrance plastic chest wall 20'. Being outside the primary beam, the exit chest wall does not show in the spectrum. Its presence is only manifested in the reduced count rates of the scattered beams.

Figure 8:
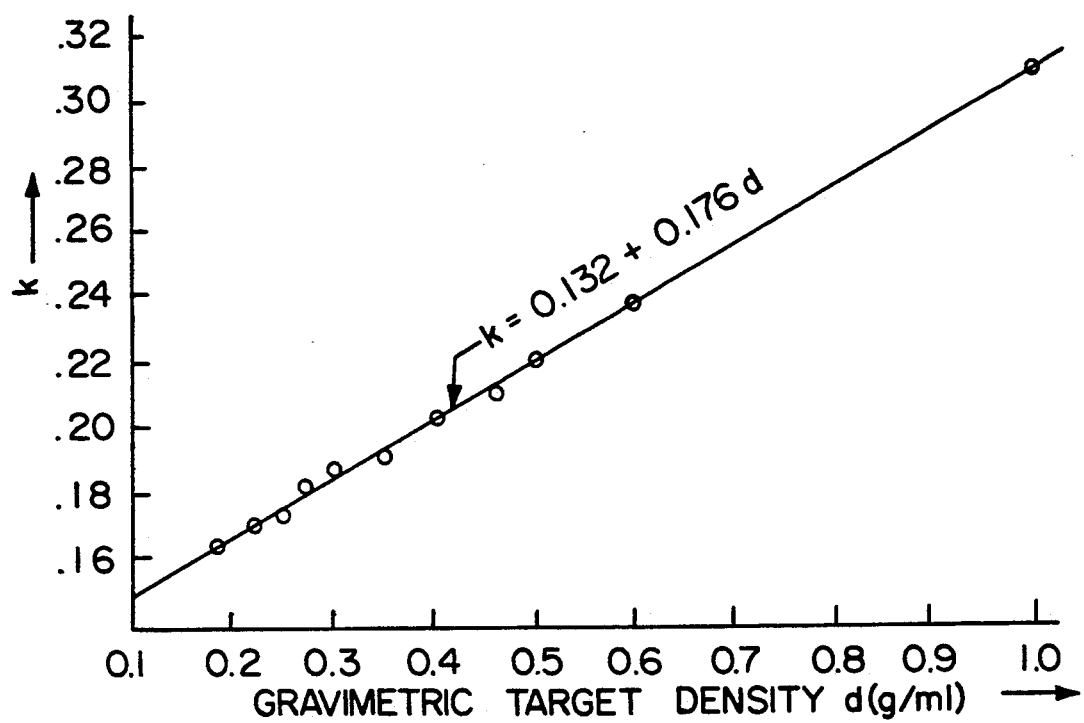
FIG. 8 is a calibration curve similar to FIG. 4 showing a relationship between the attenuation constant and the lung density for the FIG. 6 embodiment.

FIG. 5, referenced above for explaining the general principles of the present invention, shows the distributions of count rate per centimeter interval as a function of depth x for lung densities 0.25 and 0.50 g/ml. It is seen that while the 6.5 mm plastic "chest wall" has reduced the count-rate by 25%, the values of the attenuation constant k are reduced only by 2–3%. FIG. 8, which is similar to FIG. 4, shows a linear relationship between the attenuation constant k and the chest density given by the regression equation $k=0.132+0.176d$ in the range of $d=0.19$ to $1.0$ g/ml. Most of the departures of the data points from the regression line in FIG. 8 were found to be due to non-uniform packing of the sawdust in the phantom (lung 21'). The reproducibility of k is typically better than 0.5% for long counting times. Thus, for the FIG. 6 embodiment, the corresponding reproducibility in d is from 2.4% to 1.1% in the density range of 0.2 to 0.6g/ml.

To estimate the precision obtainable in a clinical situation where statistical errors are important, six measurements were made for 60 minutes each at a density of 0.3 g/ml. The result showed a standard deviation of k of 1.9, equivalent to a density error of 0.02 g/ml. If the source strength of the FIG. 6 embodiment is increased to 0.18 Curie, then the same measurement precision can be expected from a one-minute measurement on a patient. The maximum radiation dose in soft tissues from this measurement is estimated to be 1.9 mr. Thus, even if a one-Curie source is used to cope with attenuation by chest walls, the maximum dose will still be only about 10 mr over a small area of about 1cm$^2$. Therefore, a radiation risk is less than a thousandth of that from a typical hospital x-ray which may deliver up to 100 mr over the entire chest.

In summary, preliminary test results indicate that with a radioactive source less than 30 GBq (37 Giga-Becquerels =1 Curie), it should be possible to make an accurate lung density measurement in one minute with a risk of radiation exposure to the patient a thousand times smaller than that from a typical chest x-ray. This makes it possible to provide a safe, routine lung density measurement, for example, for monitoring the course of pulmonary edema at the hospital bedside or out-patient clinics, and for evaluating the efficacy of therapy in clinical research.

The description of the present invention given above should be compared in particular with the prior art Compton scattering technique. According to a typical prior setup, a target volume is defined by collimators placed in front of the radiation source and the detectors. A source is placed at the back of the patient and detectors are placed in front and, say, at the left side of the patient (or 90° from the incident beam). The front detector measures the transmitted radiation and the side detector measures the Compton-scattered radiation. A measurement is made of the ratio of the Compton-scattered radiation received by the side detector to the transmitted radiation received by the front detector. Then, in an effort to cancel the effects of wall thickness, either the apparatus or the patient is rotated by 180°. A second source whose energy is matched to that of the scattered beam is placed at the left of the patient. A second ratio of scattering (front to right) to the transmission (left to right) is measured. The product of these two ratios is in principle proportional to the square of the target density. However, the same target volume is not always duplicated after the rotation, and of course the apparatus must be larger than the width or thickness of the human body. Such extended size facilitates detection of multiply scattered photons which should not be detected, causing substantial inaccuracies in the qualitative measurement.

By contrast, the apparatus described in this specification can be very small, consisting essentially of a collimated radiation source and a single detector, and therefore the system is easily portable and can be used, for example, at the bedside of patients under intensive care. In addition, the target volume is precisely defined by the collimated incident beam and energy of the Compton-scattered photons. The use of a high resolution detector has the following two advantages. Firstly, the target lung can be defined by the energy of the photons rather than by the collimated incident beam. Secondly, multiple-scattered photons can be more easily identified and rejected.

The foregoing description of embodiments of the invention has been presented for purposes of illustration and description. It is not intended to be exhaustive or to limit the invention to the precise forms disclosed, and obviously many modifications and variations are possible in light of the above teaching. For example, any monochromatic photon source in the energy range of 100–200 keV may be used instead of Ce-139 or the Co$^{57}$ disclosed above the distance between the center of the target and the detector may be varied accordingly, say, between 5–15 cm. The shielding housing for the source may be of any suitable dense material other than lead or tantalum. The embodiments were chosen and described in order to best explain the principles of the invention and its practical application.

It is intended therefore that many changes and modifications which may be apparent to a person skilled in the art are within the scope of the present invention.

What is claimed is:

1. A non-invasive method for measuring lung density comprising the steps of:
   irradiating a target lung with a single collimated beam of monochromatic photons;
   using a single high-resolution detector, detecting photons which are Compton backscattered by the target lung;
   measuring energies of the backscattered photons;
   determining relative intensities of scattering at successive points along the collimated beam inside the target lung by comparing the intensity of each of the successive points with the intensity of each adjacent point along the collimated beam;
   determining attenuation constant of the target lung from the relative intensities; and
   determining density of the target lung from the attenuation constant.

2. The method of claim 1, wherein said irradiating step includes defining the volume of the target lung on which the collimated beam is incident thereon and the energies of Compton-scattered photons.

3. The method of claim 1, further comprising the step of carrying out the irradiating and measuring steps so that the backscattered photons show an exponential decrease in intensity as a function of depth along the beam inside the target lung.

4. The method of claim 1, wherein the irradiating step includes providing a monoenergetic photon source which produces the collimated beam of photons in the range of 100–200 keV, and locating the source within a protective housing constructed of a suitable dense material.

5. The method of claim 4, further including the step of constructing the protective housing from lead.

6. The method of claim 1, wherein the step of detecting Compton backscattered photons is carried out by utilizing high-purity germanium in the high-resolution detector.

7. The method of claim 6, wherein the measuring step includes positioning the detector in the range of 515 cm away from the center of the target lung.

8. The method of claim 6, further including the step of locating an apertured shield between the target lung and the detector for minimizing the passage of multiple-scattered photons from entering into the detector.

9. The method of claim 8, further including the step of forming the apertured shield from materials selected from the group consisting of tantalum and lead.

10. The method of claim 1, further including the step of locating an apertured shield, formed from materials selected from the group consisting of tantalum and lead, intermediate the detector and the target lung for minimizing passage of multi-scattered photons into the detector.

11. The method of claim 1, further including the step of directing the collimated beam onto the target lung at an angle of about 25°–45° with respect to a front surface of the detector.

12. The method of claim 1, further including the step of positioning the detector with respect to the collimated beam so as to form an angle therebetween in the range of about 90° to about 160°.

13. The method of claim 1, wherein the irradiating step includes providing a monoenergetic photon source selected from the group consisting of $Co^{57}$ and Ce-139 located in a lead housing.

14. The method of claim 1, wherein the irradiating step includes providing a monoenergetic photon source which produces the collimated beam of photons at an energy selected from the group consisting of 122 keV to 166 keV.

15. The method of claim 1, further including the steps of forming the collimated beam so as to have an initial diameter of 5 mm and a half-angle divergence of 50 mr, and directing the collimated beam onto the target lung so as to be at an angle $\theta$ with respect to a front surface of the detector.

16. The method of claim 1, further comprising the step of establishing a functional relationship between target lung density and attenuation constant.

17. The method of claim 1, wherein the step of determining attenuation constant includes carrying out a linear regression analysis.

18. A Compton densitometer for measuring lung density through a wall of unknown composition and thickness comprising:
source means for producing a single collimated beam of monoenergetic photons adapted for irradiating an associated target lung located behind such a wall of unknown composition and thickness;
a single high-resolution detector means for detecting Compton backscattered photons caused by irradiation of such an associated target lung located behind a wall of unknown composition and thickness with said collimated beam of photons, said detector means being positioned at an angle $\phi$ with respect to the collimated beam so as to receive backscattered photons from and angle $\theta$ with respect to the collimated beam;
an apparatus operatively connected to said detector means and including: means for measuring energies of the backscattered photons, means for determining relative intensities of scattering at successive points along the collimated beam inside such an associated target lung, means for determining attenuation constant of such an associated target lung from the relative intensities, and means for determining density of such an associated target lung from the attenuation constant when irradiated by said collimated beam of photons from said source.

19. The densitometer of claim 18, wherein said detector means is adapted to be positioned in a range of about 5–15 cm from a center of such an associated target lung to be irradiated.

20. The densitometer of claim 18, wherein said detector means consists of a high-purity germanium detector.

21. The densitometer of claim 20, wherein said detector is constructed to consist of a central region and a guard ring.

22. The densitometer of claim 18, additionally including an apertured shield positioned adjacent said detector means for minimizing passage of multiple-scattered photon into said detector means.

23. The densitometer of claim 22, wherein said apertured shield is constructed from material selected from the group consisting of tantalum and lead.

24. The densitometer of claim 18, wherein said source means is located in a shielded housing and is constructed so as to produce a collimated beam of monochromatic photons having energy in the range of 100–200 keV.

25. The densitometer of claim 24, wherein said source means is selected from the group consisting of $Co^{57}$ and Ce-139.

26. The densitometer of claim 18, wherein said source means and said detector means are positioned with respect to each other so that relative intensity of said collimated beam, as detected by said detector means and measured by said apparatus, decreases exponentially along a path inside an associated target lung.

27. The densitometer of claim 26, wherein said path is about 2–8 cm in length.

28. The densitometer of claim 18, wherein said detector means consists of a high-resolution, high-purity germanium detector having a central region and a guard ring adjacent said central region.

29. A Compton densitometer for measuring lung density comprising:
source means for producing a single collimated beam of monoenergetic photons adapted for irradiating an associated target lung;
a single high-resolution detector means for detecting Compton backscattered photons caused by irradiation of such an associated target lung with said collimated beam of photons, said detector means being positioned at an angle $\phi$ with respect to successive points along the collimated beam so as to receive backscattered photons from said successive photons at an angle $\theta$ with respect to the collimated beam;
and apparatus operatively connected to said detector means for determining the density of such an associated target lung when irradiated by said collimated beam of photons from said source, said apparatus includes preamplifier means operatively connected to receive output from said detector means having a guard ring, anti-coincidence means positioned and operatively connected to receive output from said preamplifier means, an amplifier means positioned and operatively connected to receive output from said anti-coincidence means, an ADC-MCA means positioned and operatively connected to receive output from said amplifier means, computer means operatively connected to receive output from said ADC-MCA means, and readout means operatively connected to said computer means.

30. The densitometer of claim 18, wherein said detector means consists of a high-resolution, high-purity germanium detector having a central region and a guard ring adjacent said central region.

31. A Compton densitometer for measuring density of an object located behind a wall of unknown composition and thickness comprising:

source means for producing a single collimated beam of monoenergetic photons adapted for irradiating an associated target located behind such a wall of unknown composition and thickness;

a single high-resolution detector means for detecting Compton backscattered photons caused by irradiation of such an associated target with said collimated beam of photons, said detector means being positioned at an angle $\phi$ with respect to said collimated beam so as to receive backscattered photons from an angle $\theta$ with respect to said collimated beam;

means for measuring energies of the backscattered photons;

means for determining relative intensities of scattering at successive points along said collimated beam inside such an associated target;

means for determining attenuation constant of such an associated target from the relative intensities; and means for determining density of such an associated target from the attenuation constant.

32. The densitometer of claim 31, wherein said detector means is adapted to be positioned in a range of about 5–15 cm from a center of such an associated target to be irradiated.

33. The densitometer of claim 31, wherein said source means is constructed to produce a collimated beam of monochromatic photons having energy in the range of 100–200 keV.

34. The densitometer of claim 31, wherein said source means and said detector means are positioned with respect to each other so that relative intensity of said successive points along collimated beam, as detected by said detector means, decreases exponentially along a path inside such an associated target.

35. The densitometer of claim 34, wherein said path is about 2–4 cm in length.

36. A non-invasive method for measuring density of an object located behind a wall of unknown composition and thickness comprising the steps of:

irradiating an object located behind such a wall of unknown composition and thickness with a single collimated beam of monochromatic photons;

using a single high-resolution detector, detecting photons which are Compton backscattered by the object;

measuring energies of the backscattered photons;

determining relative intensities of scattering at successive points along the collimated beam inside the object by comparing the intensity of each of the successive points with the intensity of each adjacent point along the collimated beam;

determining attenuation constant of the object from the relative intensities; and determining density of the object from the attenuation constant.

37. The method of claim 36, wherein the irradiating step includes providing a monoenergetic photon source selected from the group consisting of $Co^{57}$ and Ce-139.

* * * * *